United States Patent
Shalyt et al.

(10) Patent No.: US 11,555,798 B2
(45) Date of Patent: Jan. 17, 2023

(54) SELECTIVE MONITORING OF MULTIPLE SILICON COMPOUNDS

(71) Applicant: ECI TECHNOLOGY, INC., Totowa, NJ (US)

(72) Inventors: Eugene Shalyt, Washington Township, NJ (US); Guang Liang, Elmhurst, NY (US)

(73) Assignee: ECI TECHNOLOGY, INC., Totowa, NJ (US)

(*) Notice: Subject to any disclaimer, the term of this patent is extended or adjusted under 35 U.S.C. 154(b) by 571 days.

(21) Appl. No.: 16/585,755

(22) Filed: Sep. 27, 2019

(65) Prior Publication Data

US 2020/0110053 A1    Apr. 9, 2020

Related U.S. Application Data

(60) Provisional application No. 62/856,852, filed on Jun. 4, 2019, provisional application No. 62/742,561, filed on Oct. 8, 2018.

(51) Int. Cl.
  *G01N 27/333*    (2006.01)
  *H01L 21/306*    (2006.01)
  *G01N 33/00*    (2006.01)

(52) U.S. Cl.
  CPC ..... *G01N 27/333* (2013.01); *H01L 21/30604* (2013.01); *G01N 2033/0095* (2013.01)

(58) Field of Classification Search
  CPC ......... G01N 27/333; G01N 2031/0095; G01N 2033/0095; H01L 21/30604
  See application file for complete search history.

(56) References Cited

U.S. PATENT DOCUMENTS 8,008,087 B1    8/2011    Shalyt et al.
8,821,752 B2    9/2014    Cho et al.
(Continued)

FOREIGN PATENT DOCUMENTS

JP    H 7-86260 A    3/1995
JP    2011-203252 A    10/2011
(Continued)

OTHER PUBLICATIONS

Office Action dated Jul. 19, 2022 corresponding to Japanese Patent Application No. 2021-167038.
(Continued)

*Primary Examiner* — Alexander S Noguerola
(74) *Attorney, Agent, or Firm* — Baker Botts L.L.P.

(57) ABSTRACT

Methods and apparatuses for selective monitoring of multiple silicon compounds in etchant solutions are provided. Methods can include reacting a test solution comprising a plurality of different silicon compounds with a fluoride-based compound in several conditions to provide different silicon:reagent binding ratios. One of the conditions can include the addition of a co-solvent to the test solution. Concentrations of the multiple silicon compounds can be determined based on the different binding ratios of silicon:reagent. Methods can further include a measuring method such as silicon elemental analysis or measuring of functional groups of a certain silicon form of a first portion of a test solution comprising a plurality of different silicon compounds and reacting a second portion of the solution with a fluoride-based compound to provide a silicon:reagent binding ratio. Concentrations of the multiple silicon compounds can be determined based on the measuring method and binding ratio measurements.

28 Claims, 7 Drawing Sheets

(56) References Cited

U.S. PATENT DOCUMENTS

| | | |
|---|---|---|
| 8,940,182 B2 | 1/2015 | Hong et al. |
| 2016/0018358 A1 | 1/2016 | Shalyt et al. |

FOREIGN PATENT DOCUMENTS

| | | |
|---|---|---|
| JP | 2013-41923 A | 2/2013 |
| JP | 2015-195306 A | 11/2015 |
| TW | 201102352 A | 1/2011 |

OTHER PUBLICATIONS

Office Action dated Mar. 1, 2022 corresponding to Taiwanese Patent Application No. 108136133.

510 — Providing a test solution having a first portion and a second portion and including a predetermined volume of an etchant solution, the etchant solution including a plurality of silicon compounds 520 — Performing a measuring method of the first portion of the test solution for total silicon concentration to provide a first measurement 530 — Adding a fluoride-based compound with a predetermined volume of a co-solvent to the second portion of the test solution providing a binding ratio of silicon : reagent and performing a second measurement 540 — Determining a concentration of at least one silicon compound of the plurality of silicon compounds based on the first and second measurements

SELECTIVE MONITORING OF MULTIPLE SILICON COMPOUNDS

CROSS-REFERENCE TO RELATED APPLICATIONS

This application claims the benefit of priority to U.S. Provisional Application Ser. No. 62/742,561 filed on Oct. 8, 2018 and U.S. Provisional Application Ser. No. 62/856,852 filed on Jun. 4, 2019, the contents of which are hereby incorporated by reference in their entireties.

FIELD

The present disclosure relates to analysis of semiconductor processing solutions, and more particularly to techniques for selective monitoring of multiple silicon compounds in silicon wafer etchant solutions.

BACKGROUND

Electrodeposition processes are used in several industries including metal finishing, semiconductor, printed circuit board, and solar industries in order to deposit metal or produce products with desired properties. For example, etching processes can be used for the fabrication of both circuitry and semiconductor devices on silicon integrated circuit (IC) chips. The semiconductor industry widely employs silicon nitride ($Si_3N_4$) materials in such processes. Certain processes provide a silicon nitride ($Si_3N_4$) mask disposed on a layer of silicon dioxide ($SiO_2$) which can be patterned and etched to expose an underlying silicon/silicon dioxide layer.

The exposed silicon layer can be locally oxidized, e.g., at high temperatures (e.g., about 800° C. to about 1200° C.) to produce thicker insulating silicon dioxide ($SiO_2$) in unmasked areas in order to electrically isolate subsequently formed metal oxide semiconductor (MOS) transistors. The silicon-nitride mask can withstand high temperatures but can also require a relatively strong etchant which can also operate at high temperatures (e.g., >about 150° C.). The silicon nitride etching process should be closely controlled to provide substantially complete removal of the silicon-nitride mask material without excessive etching of the underlying silicon dioxide layer. Thus, it is important to control the etch rate of silicon nitride ($Si_3N_4$) relative to the etch rate of silicon dioxide ($SiO_2$) in such processes. In another example, the manufacturing of vertical NAND (V-NAND) memory devices can include the deposition of alternating layers of silicon dioxide ($SiO_2$) and silicon nitride ($Si_3N_4$) followed by etching of a silicon nitride ($Si_3N_4$) layer as described, for example, in U.S. Pat. No. 8,940,182 to Hong, et al. Silicon nitride ($Si_3N_4$) can also be used as an etchant in several other applications in semiconductor manufacturing.

Silicon nitride materials can be effectively etched using a high temperature phosphoric acid ($H_3PO_4$) solution. The silicon nitride etchant can be a concentrated solution of phosphoric acid (e.g., about 85 wt.-%) and can be operated at temperatures above about 150° C. (typically, e.g., at about 165° C.). The etch rate of silicon nitride ($Si_3N_4$) and its selectivity with respect to silicon dioxide ($SiO_2$) in such etchant solutions can depend on the concentration of silicon ions derived from the etching process and which can accumulate in the etchant solution during use. Silicon ions can reduce the etch rates of both silicon nitride ($Si_3N_4$) and silicon dioxide ($SiO_2$) in the phosphoric acid etchant and can also improve their selectivity. However, the electrolyte does not necessarily possess sufficient selectivity toward silicon nitride ($Si_3N_4$).

Presence of silica in the solution can reduce the etch rate for silicon nitride ($Si_3N_4$) and silicon dioxide ($SiO_2$), however, in a greater amount for silicon dioxide ($SiO_2$), thus enabling for selective etching of silicon nitride ($Si_3N_4$) in the presence of silicon dioxide ($SiO_2$). A higher concentration of silicon dioxide ($SiO_2$) can improve selectivity but can also increase potential particle defect to re-deposition silicon dioxide ($SiO_2$) (a product of silicon nitride etching) on the surface. It is therefore important that the change in the etch rates and selectivity resulting from accumulation of silicon ions and the monitoring of silica content to be considered in order to optimize the silicon nitride etching process and to provide for effective process control.

The semiconductor industry has addressed silicon dioxide solubility concerns, for example, by using certain modified silicon compounds. Such silicon compounds can include organo-silicates. U.S. Patent Application Publication No. 2016/0018358 to Shalyt, et al. describes methods for monitoring organo-silicate in process solutions. As described in U.S. Pat. No. 8,821,752 to Cho, et al., such etching solutions can include silyl phosphate compounds. For example, the etching composition can include a silyl phosphate compound, phosphoric acid, and deionized water. As described in U.S. Pat. No. 8,940,182 to Hong, et al. such etching solutions can include a silicon compound including a silicon atom, an atomic group having an amino group combined with the silicon atom, and at least two oxygen atoms combined with the silicon atom. For example, the etching solution can include such silicon compound, phosphoric acid, and ammonium ions.

Certain methods for determining silicon concentration in aqueous solutions have allowed for the measurement of total silicon in solution. U.S. Pat. No. 8,008,087 to Shalyt, et al. provides metrology for use in the analysis of the silicon concentration in phosphoric acid etchant solutions and describes a practical method for measuring low concentrations of silicon ions in silicon nitride etchant solutions comprising concentrated phosphoric acid. In this method, a predetermined concentration of fluoride ions in excess of that required to react with all of the silicon ions present in a test solution can be added and the concentration of "free" fluoride ions (i.e., those not reacted with silicon ions) can be measured, preferably using a fluoride ion specific electrode (FISE). The concentration of silicon ions can be calculated from the difference between the predetermined concentration of fluoride ions added to the test solution and the concentration of "free" fluoride ions measured for the test solution. For certain concentrated phosphoric acid etchants without additives, the method of Shalyt, et al. can provide sufficiently accurate results within a short time frame using inexpensive equipment so as to enable control of the concentration of silicon ions in the etchant solution via a "bleed and feed" approach and can further be amenable to automation and on-line process control.

As certain modified silicon compounds have been used in the industry to address the solubility of silicon dioxide ($SiO_2$) in phosphoric acid solutions and prior methods have measured total silicon in solution, there is a need for methods to determine the concentration of different silicon compounds in solutions including multiple silicon compounds in order to provide for effective process control. The production of modern semiconductor structures, for example, vertical NAND (V-NAND) memory, can require the removal of large quantities of silicon nitrate and can include the use of modified silicon compounds combined with silicon dioxide ($SiO_2$) and etch product.

Certain methods provide for measurement of the total amount of silicon in solution. However, different silicon forms can impact etch rate, etch selectivity, and particle re-deposition rate in different ways. Therefore, there is a need for an effective method to measure multiple forms of silicon in a process solution separately. It is thus desirable for processes and apparatuses suitable for use in such processes to provide for selective measurement of concentrations of different silicon compounds in solutions including multiple silicon compounds. The presently disclosed subject matter addresses these and other needs.

SUMMARY

Exemplary methods and apparatuses in accordance with the present disclosure provide for selective determination of the concentration of multiple silicon compounds in etchant solutions, such as silicon wafer etchant solutions. Specifically, in certain embodiments, the present disclosure provides for conditions for selectively varying the silicon:reagent binding ratio for a particular silicon form, e.g., a modified silicon compound. In certain embodiments, the present disclosure further provides for a measuring method of the solution, e.g., silicon elemental analysis of the solution, and measurement of a silicon:reagent binding ratio for a particular silicon compound. In particular embodiments, the measuring method includes the measurement of certain functional groups of silicon compounds in solution. Thus, in such methods, multiple silicon compounds in a same process solution can be advantageously selectively measured and monitored.

A method for determining concentrations of a plurality of silicon compounds in an etchant solution is provided. The method includes providing a test solution comprising a predetermined volume of an etchant solution. The etchant solution includes a first silicon compound and a second silicon compound. A fluoride-based compound is added to the test solution in a first condition providing a first binding ratio of silicon:reagent. A first measurement is performed. The fluoride-based compound is added to the test solution in a second condition providing a second binding ratio of silicon:reagent. A second measurement is performed. A concentration of the first silicon compound and the second silicon compound is determined based on the first and second measurements. The first silicon compound is different than the second silicon compound. The first binding ratio is different than the second binding ratio.

In certain embodiments, the fluoride-based compound can include a predetermined concentration of fluoride ions, and performing the first and second measurements can include measuring a measured concentration of fluoride ions in the test solution; and determining a silicon concentration from the difference in the predetermined and the measured concentration of the fluoride ions in the test solution.

In certain embodiments, the measuring a measured concentration of the fluoride ions can include using ion chromatography, capillary electrophoresis, or electrochemical methods.

In certain embodiments, the measuring a measured fluoride concentration of the fluoride ions can include using a fluoride ion-selective electrode.

In certain embodiments, the second condition can include adding a predetermined volume of a co-solvent to the test solution.

In certain embodiments, the co-solvent can be pre-blended with a reagent.

In certain embodiments, the co-solvent can be aqueous.

In certain embodiments, the co-solvent can include deionized water.

In certain embodiments, the co-solvent can be non-aqueous.

In certain embodiments, the co-solvent can include carboxylic acid, sulfonic acid, or a combination thereof.

In certain embodiments, the co-solvent can include acetic acid, propionic acid, Methanesuflonic acid, substituted derivatives thereof, or combinations thereof.

In certain embodiments, the test solution can include phosphoric acid present in an amount of from about 10 wt.-% to about 100 wt.-%, based on the total weight of the test solution.

In certain embodiments, the method can further include selectively etching silicon nitride with the test solution.

In certain embodiments, the method can further include selectively etching a material with the test solution to manufacture a microelectronic device.

In certain embodiments, providing the test solution can include sampling the test solution from a recirculation loop.

A method for determining concentrations of a plurality of silicon compounds in an etchant solution is provided. The method includes providing a test solution comprising a predetermined volume of an etchant solution. The etchant solution includes a first silicon compound and a second silicon compound. A fluoride-based compound is added to the test solution providing a first binding ratio of silicon:reagent. A first measurement is performed. A predetermined volume of a co-solvent is added to the test solution providing a second bonding ratio of silicon:reagent. A second measurement is performed. A concentration of the first silicon compound and the second silicon compound is determined based on the first and second measurements. The first silicon compound is different than the second silicon compound. The first binding ratio is different than the second binding ratio.

In certain embodiments, the fluoride-based compound can include a predetermined concentration of fluoride ions, and the performing the first and second measurements can include measuring a measured concentration of fluoride ions in the test solution; and determining a silicon concentration from the difference in the predetermined and the measured concentration of the fluoride ions in the test solution.

In certain embodiments, the measuring the measured concentration of the fluoride ions can include using ion chromatography, capillary electrophoresis, or electrochemical methods.

A method for determining concentrations of a plurality of silicon compounds in an etchant solution is provided. The method includes providing a test solution having a first portion and a second portion and including a predetermined volume of an etchant solution. The etchant solution includes a first silicon compound and a second silicon compound. A first measurement of the first portion of test solution is performed. The first measurement includes a total silicon concentration or a total concentration of one or more functional groups of a silicon form of the first or second silicon compound. A fluoride-based compound is added to the second portion of the test solution providing a binding ratio of silicon:reagent and a second measurement is performed. A concentration of the first silicon compound and the second silicon compound is determined based on the first and second measurements.

In certain embodiments, the fluoride-based compound can include a predetermined concentration of fluoride ions, and performing the second measurement can include measuring a measured concentration of fluoride ions in the test solution; and determining a silicon concentration from the difference in the predetermined and the measured concentration of the fluoride ions in the test solution.

In certain embodiments, the measuring a measured concentration of the fluoride ions is selected from using ion chromatography, capillary electrophoresis, or electrochemical methods.

In certain embodiments, performing the first measurement can include having equal sensitivity to all silicon forms, and performing the second measurement can include having unequal sensitivity to all silicon forms.

In certain embodiments, the method can further include diluting the first portion of the test solution prior to performing the first measurement.

An apparatus for determining concentrations of a plurality of silicon compounds in an etchant solution including phosphoric acid, silicon compounds and water. The apparatus includes an analysis cell adapted to contain a test solution including a predetermined volume of the etchant solution, a predetermined concentration of a fluoride-based reagent, and optionally a predetermined volume of a co-solvent. The apparatus further includes a reservoir fluidically coupled to the analysis cell, adapted to receive the predetermined volume of the etchant solution, the predetermined concentration of the fluoride-based reagent, and the predetermined volume of the co-solvent. The apparatus further includes a fluoride ion specific electrode and a reference electrode operatively coupled to the analysis cell for measuring the concentration of fluoride ions in the test solution. The apparatus further includes a processor having a memory element with stored instructions operative to cause, when executed, provides the predetermined volume of the etchant solution from the reservoir to the analysis cell, provides the predetermined volume of the co-solvent, if any, from the reservoir to the analysis cell, provides the predetermined concentration of the fluoride-based reagent from the reservoir to the analysis cell in stoichiometric excess at a predetermined binding ratio of that required to react with substantially all of the silicon ions in the test solution such that the fluoride ion specific electrode and the reference electrode contact with the test solution, measures a potential of the fluoride ion specific electrode, and determines the concentration of silicon ions in the etchant solution based on the difference in the measured potential and an expected potential for the predetermined concentration of the fluoride ions in the test solution.

In certain embodiments, the fluoride ion specific electrode and the reference electrode can include a combination electrode.

In certain embodiments, the fluoride ions can be added to the test solution as part of a fluoride compound.

In certain embodiments, the apparatus can further include a temperature sensor for measuring a temperature of the test solution. In certain embodiments, the processor can be further operative to acquire temperature data from the temperature sensor.

An apparatus for determining concentrations of a plurality of silicon compounds in an etchant solution including phosphoric acid, silicon compounds and water. The apparatus includes an analysis cell adapted to contain a test solution including a predetermined volume of the etchant solution and a predetermined volume of a co-solvent. The co-solvent includes a predetermined concentration of a fluoride-based compound. The apparatus further includes a reservoir, fluidically couples to the analysis cell, adapted to receive the predetermined volume of the etchant solution and the predetermined volume of the co-solvent. The apparatus further includes a fluoride ion specific electrode and a reference electrode operatively coupled to the analysis cell for measuring the concentration of fluoride ions in the test solution. The apparatus further includes a processor having a memory element with stored instructions operative to cause, when executed, provides the predetermined volume of the etchant solution from the reservoir to the analysis cell, provides the predetermined volume of the co-solvent from the reservoir to the analysis cell, the co-solvent including the predetermined concentration of the fluoride-based reagent in stoichiometric excess at a predetermined binding ratio of that required to react with substantially all of the silicon ions in the test solution such that the fluoride ion specific electrode and the reference electrode contact with the test solution, measures a potential of the fluoride ion specific electrode, and determines the concentration of silicon ions in the etchant solution based on the difference in the measured potential and an expected potential for the predetermined concentration of the fluoride ions in the test solution.

An apparatus for determining concentrations of a plurality of silicon compounds in an etchant solution comprising phosphoric acid, silicon compounds and water. The apparatus includes a first analysis cell adapted to contain a first test solution comprising a predetermined volume of the etchant solution and a predetermined volume of a co-solvent, the co-solvent comprising a predetermined concentration of a fluoride-based reagent; a second analysis cell adapted to contain a second test solution comprising a predetermined volume of the etchant solution; a reservoir, fluidically coupled to the first and second analysis cells, adapted to receive the predetermined volume of the etchant solution to the first and second test solutions; a fluoride ion specific electrode and a reference electrode operatively coupled to the first analysis cell for measuring the concentration of fluoride ions in the first test solution; an elemental analyzer operatively coupled to the second analysis cell for measuring the total silicon concentration of the second test solution; and a processor having a memory element with stored instructions operative to cause, when executed, provides the predetermined volume of the etchant solution from the reservoir to the first and second analysis cells, provides the predetermined volume of the co-solvent from the reservoir to the first analysis cell, the co-solvent comprising the predetermined concentration of the fluoride-based reagent in stoichiometric excess at a predetermined binding ratio of that required to react with substantially all of the silicon ions in the test solution such that the fluoride ion specific electrode and the reference electrode contact with the first test solution, measures a potential of the fluoride ion specific electrode, determines the concentration of silicon ions in the first etchant solution based on the measured potential and an expected potential for the predetermined concentration of the fluoride ions in the first test solution, and provides a predetermined volume of the second test solution from the second analysis cell to the elemental analyzer for elemental analysis, and determines a total silicon concentration of the second test solution.

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 3 is a flow diagram schematically illustrating a method according to the present disclosure;

DETAILED DESCRIPTION

Figure 1:
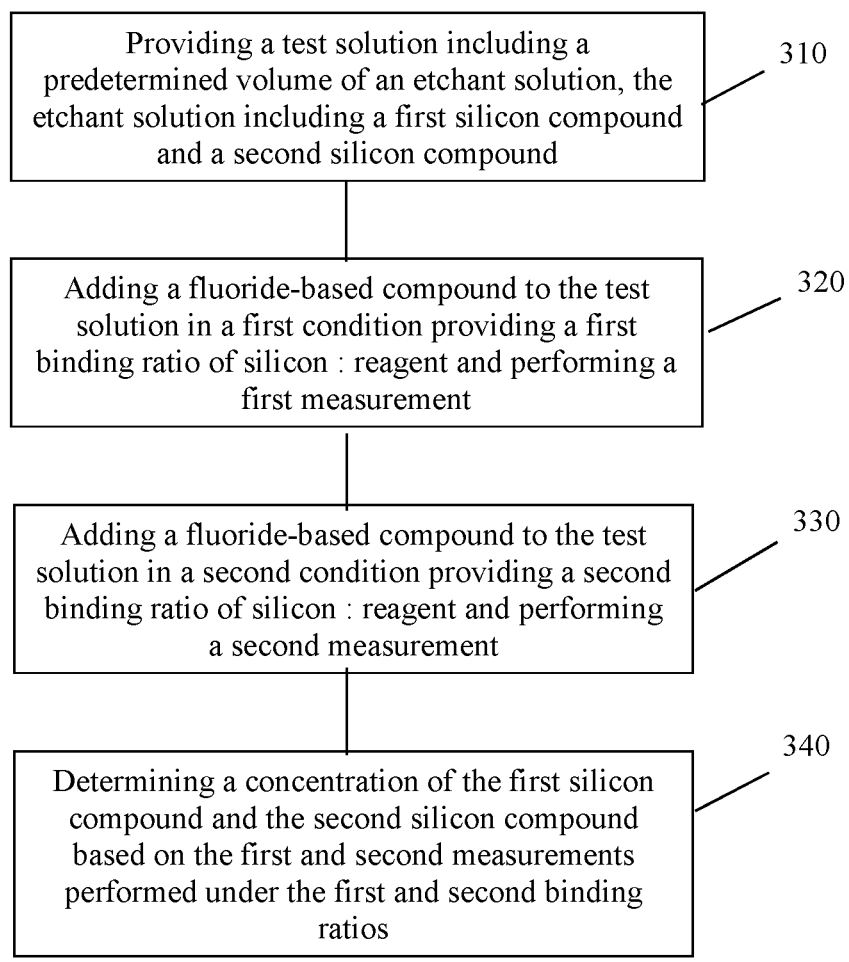
FIG. 1 is a flow diagram schematically illustrating a method according to the present disclosure.

The present disclosure provides techniques for selective monitoring of multiple silicon compounds in etchant solutions such as silicon wafer etchant solutions. In certain embodiments, the present disclosure provides for conditions in selectively varying the silicon:reagent binding ratio for a particular silicon form. The present disclosure further provides for a measuring method, e.g., an elemental analysis of the solution and measurement of a silicon:reagent binding ratio for a particular silicon form. Further, the present disclosure provides for a measuring method including the measurement of certain functional groups of silicon compounds in solution and measurement of a silicon:reagent binding ratio for a particular silicon form. Accordingly, multiple silicon compounds in a same process solution can be advantageously selectively measured and monitored.

Technical terms used in the present disclosure are generally known to those skilled in the art. The term "standard addition" generally means addition of a predetermined quantity of a species to a predetermined volume of a solution (e.g., a test solution). The predetermined quantity can be a predetermined weight of the species or a predetermined volume of a standard solution containing the species. A "standard solution" is a solution comprising a known concentration of a reagent used for chemical analysis. The symbol "M" means molar concentration. Calibration data are typically handled as calibration curves or plots, but such data can be tabulated and used directly, especially by a computer, and the terms "curve" or "plot" include tabulated data. Water used for solution preparation or dilution can include substantially pure water, deionized water or distilled water, for example.

The phrase "predetermined concentration" refers to a known, target, or optimum concentration of a component in a solution.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The present disclosure provides methods and apparatuses for selectively determining the concentration of multiple silicon compounds in solution, e.g., an etchant solution. The present disclosure can be applied to various etchant solutions including, but not limited to, the analysis of silicon nitride etchant solutions comprising a high concentration of phosphoric acid. The silicon nitride etchant solution can include about 85% phosphoric acid ($H_3PO_4$) and can be operated at a temperature of about 165° C. Operating temperatures of the etchant solution can depend in part on the percentage of phosphoric acid ($H_3PO_4$) present in solution. For example, as the percentage of phosphoric acid ($H_3PO_4$) in solution decreases, a lower operating temperature can be used, e.g., to avoid boiling. In certain embodiments, the etchant solution can include phosphoric acid ($H_3PO_4$) in an amount of at least about 10%, at least about 25%, at least about 50%, at least about 80%, at least about 85%, at least about 90%, or at least about 95%. In particular embodiments, the etchant solution can include phosphoric acid ($H_3PO_4$) in an amount of from about 80% to about 95%, from about 80% to about 90%, from about 80% to about 85%, about 80%, about 85%, about 90%, or about 95%. In certain embodiments, the etchant solution can be operated at a temperature of at least about 150° C., at least about 155° C., or at least about 160° C. In particular embodiments, the etchant solution can be operated at a temperature of from about 150° C. to about 200° C., from about 160° C. to about 175° C., from about 150° C. to about 170° C., or about 150° C., about 155° C., about 160° C., or about 165° C. A person skilled in the art will appreciate that a wide variety of silicon etchant solutions, e.g., with various concentrations of components and various operating temperatures, are suitable for use with the present disclosure.

An exemplary method of the present disclosure can include performing a fluoride analysis. The fluoride analysis can include reacting substantially all of the silicon ions in the etchant solution with fluoride ions added in stoichiometric excess. The method can further include measuring the concentration of the unreacted fluoride ions, e.g., via a fluoride ion specific electrode (ISE). The method can further include repeating the fluoride analysis in several different conditions, each yielding a different predetermined binding ratio of silicon:reagent. In each condition, the concentration of the total silicon in solution can be measured. One of the conditions can include the addition of a co-solvent to the process solution. From the different binding ratios of silicon:reagent and measurements obtained under such conditions, the concentrations of the multiple silicon compounds can be independently determined. Thus, multiple silicon compounds can advantageously be selectively measured and monitored in a same process solution. The method of the present disclosure can be applied to analyze different silicon forms in etchant solutions used to etch materials other than silicon nitride, e.g., silicon dioxide.

The present disclosure further provides for certain conditions to vary the silicon:reagent binding ratio for various silicon forms. Measurements of silicon concentrations under each condition having a different predetermined binding ratio can be used to determine the concentration of different silicon forms in solution. Thus, selective measurement of each silicon form in solution can be determined through a dual process or a single multi-part process including measurement under analytical conditions providing a silicon:reagent binding ratio and measurement under modified analytical conditions providing a modified silicon:reagent binding ratio. In a dual process, the silicon:reagent binding ratio can be predetermined and the etchant solution can be measured for silicon concentration without a co-solvent. A second silicon concentration measurement can be performed in a condition having a different silicon:reagent binding ratio in the etchant solution, for example, with the presence of a co-solvent which provides for a modified silicon:reagent binding ratio. Alternatively, a single multi-part process can be performed in which the silicon concentration can be measured at a predetermined the silicon:reagent binding ratio of the etchant solution without a co-solvent, a co-solvent can be added to the etchant solution, and an additional measurement of the silicon concentration under the modified silicon:reagent binding ratio can be determined. Accordingly, selective measurement of two different forms of a silicon compound can be measured in a same process solution. In certain embodiments, the silicon:reagent binding ratios can be determined through fluoride analysis as discussed in further detail below. In certain embodiments, the silicon:reagent binding ratios under each condition can be predetermined.

In certain embodiments, an exemplary method of the present disclosure provides for performing one or more measuring methods, e.g., elemental analysis methods and reacting the solution with a reagent to provide a silicon:reagent binding ratio for various silicon forms. In certain embodiments, the one or more silicon compounds in solution can have a fixed silicon:reagent binding ratio. In particular embodiments, all silicon compounds in solution can have a fixed silicon:reagent binding ratio. For example, in certain embodiments, the one or more silicon compounds can have a silicon:reagent binding ratio unaltered by experimental conditions. In particular embodiments, the solution can include one or more silicon compounds having different silicon:reagent binding ratios in which each silicon:reagent binding ratio can be unaltered by experimental conditions. For example, and not by way of limitation, the solution can include a first silicon compound having a first silicon:reagent binding ratio and a second silicon compound having a second silicon:reagent binding ratio different from the first silicon:reagent binding ratio. In such embodiments, each of the first and second silicon:reagent binding ratios can be unalterable by experimental conditions and therefore "fixed". The one or more measuring methods, e.g., elemental analysis methods can digest a solution chemical to individual atoms and provide a total concentration of an element, such as silicon, with equal sensitivity to all silicon forms. In such methods, a silicon:reagent binding ratio measuring analysis having unequal sensitivity to different silicon forms can be used to determine individual forms of silicon compounds in solution. Accordingly, selective measurement of two different forms of a silicon compound can be measured in a same process solution. In certain embodiments, the one or more measuring methods can include can include methods for measuring certain functional groups of silicon compounds.

FIG. 1 is a flow diagram schematically illustrating a method 300 according to the present disclosure. The present disclosure provides methods for selectively determining a concentration of multiple silicon compounds in a solution. In an exemplary embodiment, a test solution including a predetermined volume of an etchant solution can be provided. The etchant solution can include a plurality of silicon compounds, for example, a first silicon compound and a second silicon compound 310. A fluoride-based compound can be added to the test solution in a first condition providing a first binding ratio of silicon:reagent 320. A first measurement of the test solution can be performed. The fluoride-based compound can be added to the test solution in a second condition providing a second binding ratio of silicon:reagent 330. A second measurement of the test solution can be performed. A concentration of the first silicon compound and the second silicon compound can be determined based on the first and second measurements performed under the conditions of the first and second binding ratios 340. The first silicon compound can be different than the second silicon compound. The first binding ratio can be different than the second binding ratio.

Figure 2:
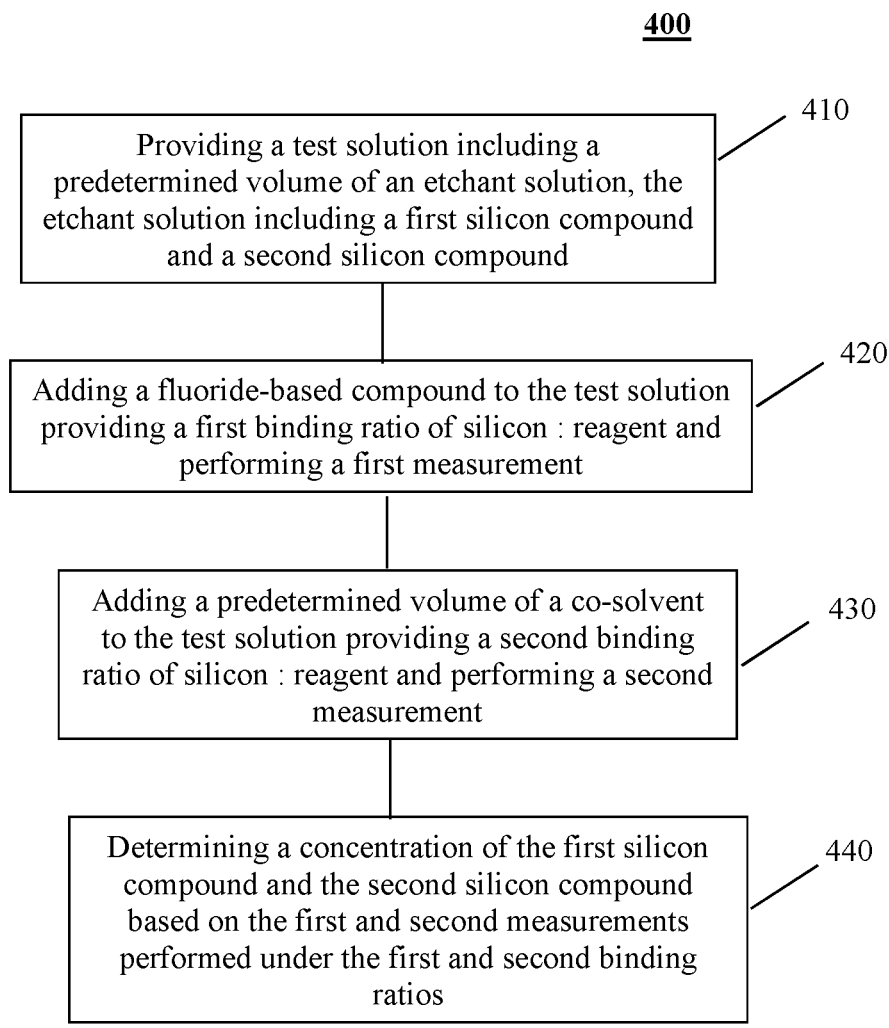
FIG. 2 is a flow diagram schematically illustrating a method according to the present disclosure.

FIG. 2 is a flow diagram schematically illustrating a method 400 according to the present disclosure. The present disclosure provides methods for selectively determining a concentration of multiple silicon compounds in a solution. In an exemplary embodiment, a test solution including a predetermined volume of an etchant solution can be provided. The etchant solution can include a plurality of silicon compounds, for example, a first silicon compound and a second silicon compound 410. A fluoride-based compound can be added to the test solution providing a first binding ratio of silicon:reagent 420. A first measurement of the test solution can be performed. A predetermined volume of a co-solvent can be added to the test solution providing a second binding ratio of silicon:reagent 430. A second measurement of the test solution can be performed. A concentration of the first silicon compound and the second silicon compound can be determined based on the first and second measurements performed under the conditions of the first and second binding ratios 440. The first silicon compound can be different than the second silicon compound. The first binding ratio can be different than the second binding ratio.

FIG. 3 is a flow diagram schematically illustrating an exemplary method 500 according to the present disclosure. The present disclosure provides methods for selectively determining a concentration of multiple silicon compounds in a solution. In an exemplary embodiment, a test solution including a predetermined volume of an etchant solution can be provided. The etchant solution can include a plurality of silicon compounds, for example, a first silicon compound and a second silicon compound 510. In particular embodiments, the first silicon compound and the second silicon compound can be different compounds. In certain embodiments, the test solution can have a first portion and a second portion. A measurement method can be performed on the first portion of the test solution, for example, to measure a total silicon concentration and provide a first measurement 520. In certain embodiments, the measurement method can be performed on the first portion of the test solution after pre-treatment of the first portion. Pre-treatment can include, for example, dilution of the test solution. In certain embodiments, pre-treatment of the first portion of the test solution can include predilution with water. In particular embodiments, the first portion of the test solution can be prediluted to about 1/2 to about 1/1000, or about 1/10. In alternate embodiments, the test solution can be provided for the measurement method without pre-treatment. One or more fluoride-based compounds can be added to the second portion of the test solution providing a binding ratio of silicon:reagent 530 and a second measurement of the test solution can be performed. In certain embodiments, the measuring method of the first portion of the test solution and the reaction of the second portion of the test solution with one or more fluoride-based compounds can be in a same analytical cell. In alternate embodiments, the measuring method of the first portion of the test solution and the reaction of the second portion of the test solution with one or more fluoride-based compounds can be in different analytical cells. A concentration of the first silicon compound and the second silicon compound can be determined based on the first and second measurements 540.

Figure 4:
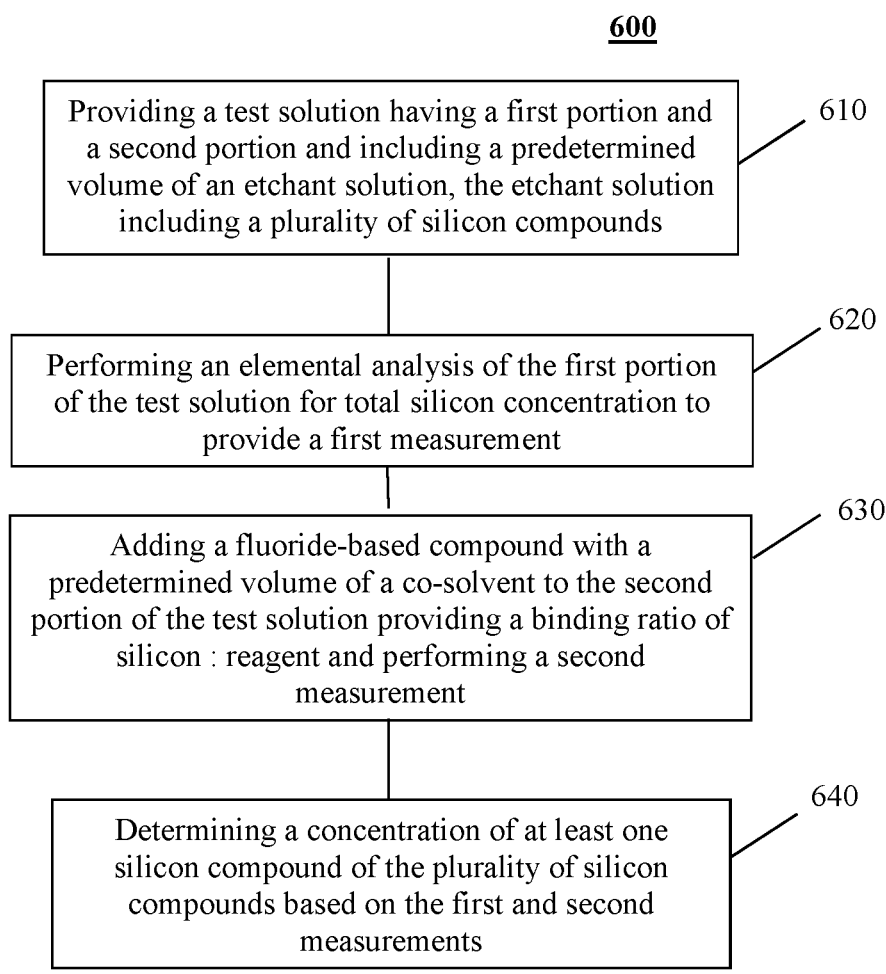
FIG. 4 is a flow diagram schematically illustrating a method according to the present disclosure.

FIG. 4 is a flow diagram schematically illustrating an exemplary method 600 according to the present disclosure. The present disclosure provides methods for selectively determining a concentration of multiple silicon compounds in a solution. In an exemplary embodiment, a test solution including a predetermined volume of an etchant solution can be provided. The etchant solution can include a plurality of silicon compounds, for example, a first silicon compound and a second silicon compound 610. In particular embodiments, the first silicon compound and the second silicon compound can be different compounds. In certain embodiments, the test solution can have a first portion and a second portion. An elemental analysis can be performed on the first portion of the test solution, for example, to measure a total silicon concentration and provide a first measurement 620. In certain embodiments, the elemental analysis can be performed on the first portion of the test solution after pre-treatment of the first portion. Pre-treatment can include, for example, dilution of the test solution. In certain embodiments, pre-treatment of the first portion of the test solution can include predilution with water. In particular embodiments, the first portion of the test solution can be prediluted to about 1/2 to about 1/1000, or about 1/10. In alternate embodiments, the test solution can be provided for elemental analysis without pre-treatment. One or more fluoride-based compounds can be added to the second portion of the test solution providing a binding ratio of silicon:reagent 630 and a second measurement of the test solution can be performed. In certain embodiments, the elemental analysis of the first portion of the test solution and the reaction of the second portion of the test solution with one or more fluoride-based compounds can be in a same analytical cell. In alternate embodiments, the elemental analysis of the first portion of the test solution and the reaction of the second portion of the test solution with one or more fluoride-based compounds can be in different analytical cells. A concentration of the first silicon compound and the second silicon compound can be determined based on the first and second measurements 640.

In certain embodiments, the measuring method can include elemental analysis, e.g., an elemental analysis of a total silicon concentration, an elemental analysis of total carbon concentration and derivatives of thereof (e.g., total organic carbon, total inorganic carbon, and total non-purgeable organic carbon), an elemental analysis of total nitrogen concentration and derivatives thereof (e.g., ammonia, organic nitrogen, and reduced nitrogen), or an elemental analysis of total sulfur concentration and derivatives thereof, or the like. In certain embodiments, the measuring method can include methods for measuring certain functional groups of silicon compounds. For example, and not by way of limitation, the measuring method can include ultraviolet-visible near-infrared/infrared spectroscopy (UV-Vis-NIR-IR), Raman spectroscopy, potentiometry, voltammetry, surface tension, or chromatography. A person skilled in the art will appreciate a wide variety of measuring methods are suitable for use with the present disclosure.

In certain embodiments, elemental analysis can be performed by, for example, AAS/AES atomic absorbance and atomic emission spectroscopy, ICP-OES/ICP-AES inductively coupled plasma with a mass-spectroscopy defector, or MP-microwave plasma. A person skilled in the art will appreciate a wide variety of elemental analysis methods are suitable for use with the present disclosure.

In certain embodiments, one or more further methods can be performed on the etchant solution in addition to the methods of the present disclosure. For example, and not by way of limitation, such methods can further characterize the etchant solution, e.g., by particle characterization (e.g., by count, size, or chemical composition) or dissolved contaminant characterization (e.g., by identification of the contaminant or concentration of the contaminant). A person skilled in the art will appreciate a wide variety of further methods on etchant solutions can be used in combination with the present disclosure.

The predetermined volume of the etchant solution can be provided manually, using a syringe, a volumetric flask, or a graduated cylinder, for example, or automatically via an automatic syringe or a metering pump, for example. The etchant solution can include one or more silicon compounds. For example, the etchant solution can include one or more of an organo-silicate, inorganic silicate, or silicon dioxide. In certain embodiments, the etchant solution includes different silicon compounds. For example, in certain embodiments, the etchant solution can include silicon dioxide and an organo-silicate.

In certain embodiments, the etchant solution can include phosphoric acid. In certain embodiments, the one or more silicon compounds can be present in phosphoric acid (e.g., 10-100 wt.-% phosphoric acid). In certain embodiments, the phosphoric acid including one or more silicon compounds can be used for selective etching of silicon nitrate. In particular embodiments, the phosphoric acid including one or more silicon compounds can be used for selective etching and manufacturing of a microelectronic device.

The one or more fluoride-based compounds can include a solid compound of known weight and can include a predetermined concentration of fluoride ions. Alternatively, a predetermined concentration of fluoride ions can be added to the test solution, for example, as a predetermined volume of a standard fluoride solution. Fluoride ions can be added as part of any fluoride compound that tends to dissociate in aqueous solution, e.g., HF, LiF, NaF, KF, $NH_4HF_2$, $NH_4F$, TMAF, TEAF and mixtures thereof. In adding the fluoride-based compound to the test solution, the concentration of fluoride ions in the test solution can be measured by any suitable mechanism. In certain embodiments, the concentration of fluoride ions can be measured using a fluoride ion specific electrode (ISE). For example, the fluoride ions can be measured by ion chromatography, capillary electrophoresis, or electrochemical methods. The fluoride ions can be measured in the test solution, e.g., by placing a fluoride ion specific electrode (ISE) and a reference electrode in contact with the test solution and measuring the potential of the fluoride ISE relative to the reference electrode. In certain embodiments, the fluoride ISE and the reference electrode can be separate electrodes. In alternate embodiments, the fluoride ISE and the reference electrode can be combined in a combination electrode.

In certain embodiments, the test solution can further include a predetermined volume of a co-solvent. The predetermined volume of the co-solvent can be provided manually, using a syringe, a volumetric flask, or a graduated cylinder, for example, or automatically via an automatic syringe or a metering pump, for example. The presence of a co-solvent can create competing conditions for fluorination and can modify the silicon:reagent binding ratio (e.g., from 1:2 to 1:1). Thus, the presence of a co-solvent can provide a modified silicon:reagent binding ratio. In certain embodiments, the co-solvent can be aqueous. In alternative embodiments, the co-solvent can be non-aqueous. The co-solvent can be an individual chemical or pre-blended with a reagent. In certain embodiments, the co-solvent can include water, for example, deionized water. In certain embodiments, the co-solvent can include carboxylic acid, sulfonic acid, or a combination thereof. For example, the test solution can further include a co-solvent selected from the group consisting of acetic acid, propionic acid, Methanesulfonic acid, substituted derivatives thereof, and combinations thereof.

In certain embodiments, a silicon:reagent binding ratio of the test solution can be different than a silicon:reagent binding ratio of the test solution in the presence of a co-solvent. In certain embodiments, the silicon:reagent binding ratio can be about 1:2 or about 1:1. In particular embodiments, the silicon:reagent binding ratio can be about 1:6, about 1:5, about 1:4, or about 1:3.

The concentration of the multiple silicon compounds in the test solution can be determined from the silicon concentration measured in different silicon:reagent binding ratio conditions which can be obtained by providing the test solution with and without the presence of a co-solvent. Analytical methods used herein are based, in part, on the disclosure of U.S. Pat. No. 8,008,087 to Shalyt, et al. Analytical methods of the present disclosure can be based on the reaction of silicon compounds with a fluoride-based reagent.

$$Si—R1(R2,R3,R4)+xRF \rightarrow SiFxRy$$

For $SiO_2/Si(OH)_4$, all four Si—OH chemical bonds can be substituted by fluoride.

$$Si(OH)_4+4RF \rightarrow SiF_4+4R—OH$$

Silicon compounds other than silicon dioxide, such as organo-silicates typically can have stronger molecular bonds and can prevent quadruple fluorination.

For example, in $Si—R1(R2,R3,R4)+2\ RF \rightarrow SiF_2—R1, R2+R—R3+R—R4$, in which only two bonds are fluorinated. As provided above, the addition of a co-solvent in the test solution can provide for competing conditions for fluorination and changes a silicon:reagent binding ratio in solution (e.g., from about 1:2 to about 1:1).

$$Si—R1(R2,R3,R4)+RF \rightarrow SiF—R1,R2,R3+R—R4$$

The selective measurement of each silicon form in the test solution can be determined as provided in Equations 1-4.

$$T_1 = Si_a + g_1 * Si_b \quad (1)$$

$$T_2 = Si_a + g_2 * Si_b \quad (2)$$

$$Si_b = (T_1 - T_2)/(g_1 - g_2) \quad (3)$$

$$Si_a = T_1 - g_1 * Si_b \quad (4)$$

where $T_1$ is the total silicon (Si) concentration under standard conditions (i.e., a first condition), $T_2$ is the total silicon (Si) concentration under modified conditions (e.g., in the presence of co-solvent as a second condition), $Si_a$ is the silicon (Si) concentration of silicon (Si) from silicon dioxide $(SiO_2)$, $Si_b$ is the silicon (Si) concentration of silicon (Si) from an alternate silicon compound, $g_1$ is the fluoride (F) binding ratio of the alternate silicon compound/fluoride (F) binding ratio of silicon dioxide $(SiO_2)$ under standard conditions (i.e., the first condition), and $g_2$ is the fluoride (F) binding ratio of the alternate silicon (Si) compound/fluoride (F) binding ratio of silicon dioxide $(SiO_2)$ under modified conditions (e.g., in the presence of co-solvent as the second condition).

In certain embodiments, the test solution can further include a predetermined volume of water. Water can be added, e.g., to dilute the etchant in the test solution. Dilution of a phosphoric acid etchant used to etch silicon nitride can improve the reproducibility and linearity of the fluoride ISE response. In certain embodiments, the fluoride-based compound can be dissolved in the added water to provide a standard fluoride ion solution such that a predetermined concentration of fluoride ions can be added to the test solution as part of the predetermined volume of added water. Alternatively, at least a portion of the predetermined volume of water added to dilute the phosphoric acid in the test solution can be added as substantially pure water.

Figure 5:
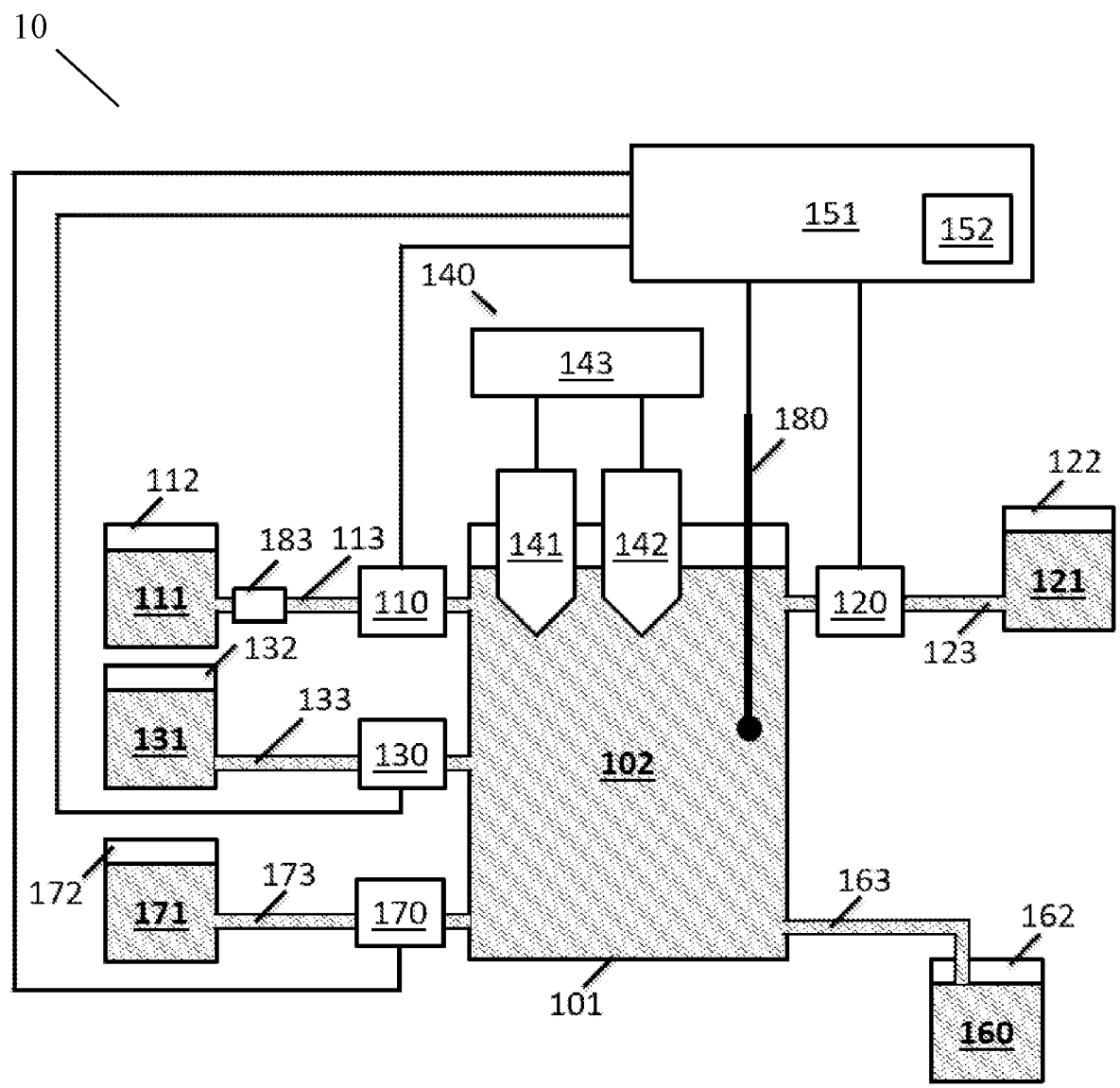
FIG. 5 schematically illustrates an apparatus of the present disclosure for determining concentrations of a plurality of silicon compounds in a phosphoric acid etchant solution.

FIG. 5 schematically illustrates an exemplary apparatus 10 of the present disclosure for determining concentrations of a plurality of silicon compounds in an etchant solution 111. The apparatus 10 can include an analysis cell 101 containing a test solution 102. The test solution 102 can include a predetermined volume of the etchant solution 111 and a predetermined concentration of a fluoride-based reagent 131. The test solution 102 can further include a predetermined volume of a co-solvent 171 (alone or pre-blended with a fluoride-based reagent). The apparatus 10 can also include a mechanism 110 for providing the predetermined volume of etchant solution 111 contained in an etchant container 112 to the test solution 102; a mechanism 130 for adding the predetermined concentration of fluoride-based reagent (e.g., a standard fluoride solution) 131 to the test solution 102; and a mechanism 170 for adding the predetermined concentration of the co-solvent 171 (alone or pre-blended with a fluoride-based reagent) to the test solution 102. In certain embodiments, the etchant container can 112 can comprise a reservoir fluidically coupled to the analysis cell 101 and adapted to receive the predetermined volume of the etchant solution to the test solution. A further mechanism 140 can be provided to measure the concentration of fluoride ions in the test solution 102. A computing device 151 having a memory element 152 can be provided with stored instructions operative to effect, via appropriate mechanical and electrical interfacing, the above mentioned providing of the test solution 102: addition of fluoride-based reagent 131 to the test solution 102, measurement of fluoride ions in the test solution 102 and determination of the silicon concentration in the etchant solution 111 from the difference in the predetermined and the measured concentrations of fluoride ions in the test solution 102. The analysis cell 101 can be of any suitable shape, including an open beaker or a closed cell with feedthroughs for the electrodes (as shown in FIG. 5), for example, and may include any suitable material, glass or a polyolefin plastic, for example.

In certain embodiments, a portion of the test solution can be provided for elemental analysis via a delivery device. The portion of the test solution can be provided without pre-treatment or can alternatively be pre-treated in an analytical cell prior to elemental analysis. Pre-treatment can include, for example, dilution of the portion of the test solution. In certain embodiments, the diluent can include water. In particular embodiments, the portion of the test solution can be diluted to a predilution ratio of about 1/2 to about 1/1000, or about 1/10. In certain embodiments, the portion of the test solution can be pre-treated in the analysis cell 101. In alternative embodiments, the portion of the test solution can be pre-treated in an analysis cell different than the analysis cell 101. Non-limiting embodiments of such apparatuses are provided in FIGS. 6A-6C and discussed in further detail below.

Figure 6A:
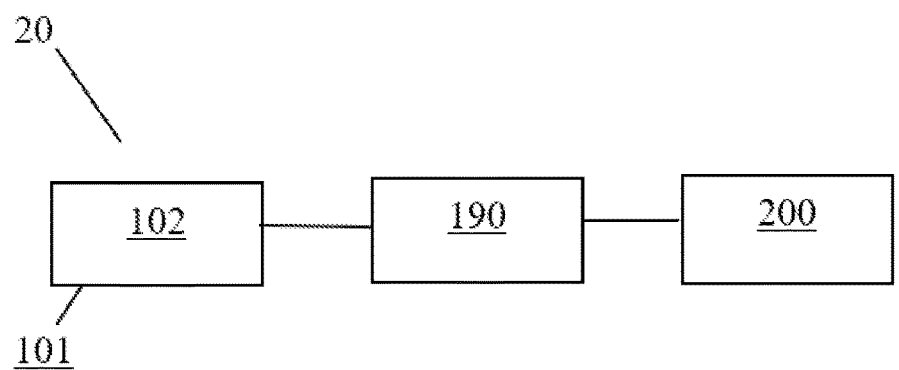
FIG. 6A schematically illustrates an apparatus of the present disclosure for determining concentrations of a plurality of silicon compounds in a phosphoric acid etchant solution including an elemental analysis of the solution.

FIG. 6A schematically illustrates an exemplary apparatus 20 of the present disclosure for determining concentrations of a plurality of silicon compounds in an etchant solution. The apparatus 20 can include an analysis cell 101 containing a test solution 102. The test solution 102 can include a predetermined volume of the etchant solution. In certain embodiments, the test solution 102 can include a first portion and a second portion. The first portion and the second portion of the etchant solution can be provided in a same analysis cell 101. The apparatus 20 can further include a device 190 coupled to the analysis cell 101. The device 190 can be configured to deliver the first portion of the test solution 102 to an elemental analyzer 200. The elemental analyzer 200 can be coupled to the device 190. The elemental analyzer 200 can be configured to perform an elemental analysis of the first portion of the test solution 102, for example, for a concentration of total silicon. In certain embodiments, the first portion of the test solution 102 can be pre-treated prior to elemental analysis in the elemental analyzer 200. In alternative embodiments, elemental analysis can be performed on the first portion of the test solution 102 without pre-treatment thereof. One or more fluoride-based compounds can be added to the second portion of the test solution 102 and a binding ratio of silicon:reagent can be measured. In alternative embodiments, the elemental analyzer 200 can be configured to perform a measuring method of the first portion of the test solution. In certain embodiments, the measuring method can include methods for measuring certain functional groups of silicon compounds.

Figure 6B:
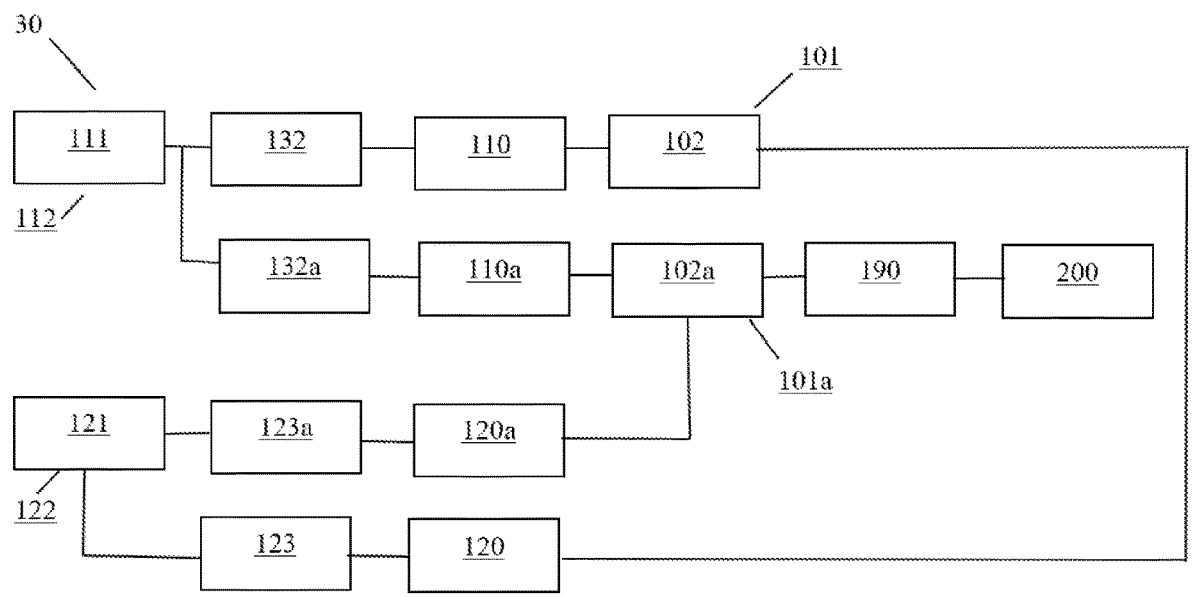
FIG. 6B schematically illustrates an apparatus of the present disclosure for determining concentrations of a plurality of silicon compounds in a phosphoric acid etchant solution including an elemental analysis of the solution.

FIG. 6B schematically illustrates an exemplary apparatus 30 of the present disclosure for determining concentrations of a plurality of silicon ions in an etchant solution. The apparatus 30 can include at least one analysis cell. In certain embodiments, the apparatus 30 can include a first analysis cell 101 and a second analysis cell 101a. The first analysis cell 101 can include a first test solution 102. The second analysis cell 101a can include a second test solution 102a. In certain embodiments, the first test solution 102 and the second test solution 102a can be a same solution. In certain embodiments, each of the first and second analysis cells 101 and 101a can include a predetermined volume of an etchant solution 111 contained in an etchant container 112. The apparatus 30 can further include a first device 110 and a second device 110a for providing a predetermined amount of the etchant solution 111 to the first and second analysis cells 101 and 101a. In certain embodiments, the etchant solution 111 can be provided from a first reservoir 132 and a second reservoir 132a which are each coupled to the etchant container 112 and configured to receive and store the etchant solution 111. The first reservoir 132 can be coupled to the first device 110 which can be coupled to the first analysis cell 101. The second reservoir 132a can be coupled to the second device 110a which can be coupled to the second analysis cell 101a.

In certain embodiments, the apparatus 30 can further include a device 190 coupled to the second analysis cell 101a including the second test solution 102a. The device 190 can be configured to deliver the second test solution 102a to an elemental analyzer 200. The elemental analyzer 200 can be coupled to the device 190. The elemental analyzer 200 can be configured to perform an elemental analysis of the second test solution 102a, for example, for a concentration of total silicon. In certain embodiments, the second test solution 102a can be pre-treated prior to elemental analysis in the elemental analyzer 200. In alternative embodiments, elemental analysis can be performed on the second test solution 102a without pre-treatment thereof. One or more fluoride-based compounds can be added to the first test solution 102 in the first analysis cell 101 and a binding ratio of silicon:reagent can be measured. Thus, in particular embodiments, the apparatus 30 can provide one or more analysis cells in which the solution is provided in different analysis cells. In alternative embodiments, the elemental analyzer 200 can be configured to perform a measuring method of the first portion of the test solution. In certain embodiments, the measuring method can include methods for measuring certain functional groups of silicon compounds.

In certain embodiments, the apparatus 30 can further include one or more dilution devices for the addition of pure water. The one or more dilution devices can be operative to provide a metered flow of water 121 from a water reservoir 122 to the analysis cell 101, 101a so as to provide a predetermined volume fraction of water 121 to the test solution 102, 102a. For automatic delivery of water 121, the one or more dilution devices can be connected, for example, to one or more pipes 123 running between the water reservoir 122 and the first and second analysis cells 101, 101a. In particular embodiments, the apparatus 30 can include a first dilution device 120 and a second dilution device 120a. The first dilution device 120 can be coupled to the first analysis cell 101. The second dilution device 120a can be coupled to the second analysis cell 101a. In particular embodiments, the apparatus 30 can include a first pipe 123 and a second pipe 123a. The first and second pipes 123, 123a can be coupled to the water reservoir 122. The first pipe 123 can be coupled to the first dilution device 120 coupled to the first analysis cell 101. The second pipe 123a can be coupled to the second dilution device 120a coupled to the second analysis cell 101a.

Figure 6C:
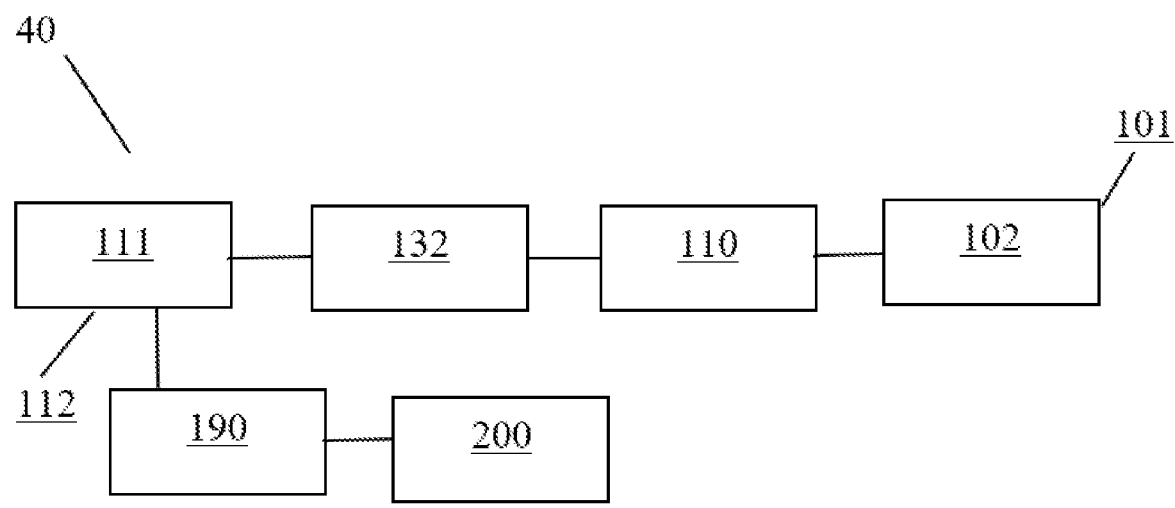
FIG. 6C schematically illustrates an apparatus of the present disclosure for determining concentrations of a plurality of silicon compounds in a phosphoric acid etchant solution including an elemental analysis of the solution.

FIG. 6C schematically illustrates an exemplary apparatus 40 of the present disclosure for determining concentrations of a plurality of silicon ions in an etchant solution. The apparatus 40 can include an analysis cell 101 containing a test solution 102. The test solution 102 can include a predetermined volume of the etchant solution 111 contained in an etchant container 112. The apparatus 40 can further include a first device 110 for providing a predetermined amount of the etchant solution 111 to the first analysis cell 101. In certain embodiments, the etchant solution 111 can be provided from a reservoir 132 coupled to the etchant container 112 and configured to receive and store the etchant solution 111. The first reservoir 132 can be coupled to the device 110 which can be coupled to the analysis cell 101. In certain embodiments, the analysis cell can be provided with a first portion of etchant solution 111. The apparatus 40 can further include a device 190 coupled to the etchant container 112. The device 190 can be configured to deliver a second portion of the etchant solution 111 to an elemental analyzer 200. The elemental analyzer 200 can be coupled to the device 190. The elemental analyzer 200 can be configured to perform an elemental analysis of the second portion of the etchant solution 111, for example, for a concentration of total silicon. Thus, in certain embodiments, the test solution 102 is not pre-treated prior to elemental analysis. One portion is directed to fluoride analysis cell 101. One or more fluoride-based compounds can be added to the test solution 102 contained in the first analysis cell 101 and a binding ratio of silicon:reagent can be measured. In alternative embodiments, the elemental analyzer 200 can be configured to perform a measuring method of the first portion of the test solution. In certain embodiments, the measuring method can include methods for measuring certain functional groups of silicon compounds.

Suitable mechanisms 110 for providing the predetermined volume of etchant solution 111 contained in an etchant container 112 to the test solution 102 in the analysis cell 101 can include a syringe, a volumetric flask or a graduated cylinder, for example, for manual delivery, or an automatic syringe or a metering pump with associate plumbing and wiring, for example, for automatic delivery (e.g., as indicated in FIG. 5). Delivery of the predetermined volume of etchant solution 111 can also be performed up to a preset level detected by an automatic level sensor. The etchant container 112 can be a production etchant tank or an etchant reservoir. For automatic delivery of the etchant solution 111, the mechanism 110 can be connected, for example, to a pipe 113 running between the etchant container 112 and the analysis cell 101.

A fluoride-based reagent can be added to the test solution 102 as part of any suitable fluoride compound that tends to dissociate in aqueous solution, HF, LiF, NaF, $NH_4HF_2$, $NH_4F$, TMAF, TEAF, etc., and mixtures thereof, for example. The predetermined concentration of fluoride-based reagent can be added to the test solution 102 as part of a solid compound of known weight, or as a predetermined volume of a standard fluoride solution 131 contained in a reagent reservoir 132 (e.g., as indicated in FIG. 5). Addition of the predetermined concentration of fluoride ions via a standard fluoride-based reagent solution is preferred since reagents are generally more easily handled as liquids, and dilution of the etchant solution tends to provide more reproducible fluoride ISE measurements in any case.

Suitable mechanisms 170 for providing the predetermined volume of co-solvent 171 (alone or pre-blended with a fluoride-based reagent) contained in a container 172 to the test solution 102 in the analysis cell 101 can include a syringe, a volumetric flask or a graduated cylinder, for example, for manual delivery, or an automatic syringe or a metering pump with associate plumbing and wiring, for example, for automatic delivery (as indicated in FIG. 5). Delivery of the predetermined volume of co-solvent 171 can also be performed up to a preset level detected by an automatic level sensor. The container 172 can be a reservoir. For automatic delivery of the co-solvent 171, the mechanism 170 can be connected, for example, to a pipe 173 running between the container 172 and the analysis cell 101.

Suitable mechanisms 130 for providing the predetermined volume of the standard fluoride solution 131 from the reagent reservoir 132 to the test solution 102 in the analysis cell 101 can include a syringe, a volumetric flask or a graduated cylinder, for example, for manual delivery, or an automatic syringe or a metering pump with associated plumbing and wiring, for example, for automatic delivery (e.g., as indicated in FIG. 5). Delivery of the predetermined volume of the standard fluoride solution 131 can also be performed up to a preset level detected by an automatic level sensor. For automatic delivery of the standard fluoride solution 131, the mechanism 130 can be connected, for example, to a pipe 133 running between the reagent reservoir 132 and the analysis cell 101.

The predetermined concentration of added fluoride ions and a predetermined dilution ratio of etchant solution 111 in the test solution 102 can be provided by addition of any suitable combination of solid fluoride compound, standard fluoride containing reagent solution, and solvent, e.g. water. Pure water can be added, for example, so that the reagent solution can be provided as a concentrate to minimize shipping and handling costs. For addition of pure water, the apparatus may further include: a dilution device 120 operative to provide metered flow of water 121 from a water reservoir 122 to the analysis cell 101 so as to provide a predetermined volume fraction of water 121 to the test solution 102. The dilution device 120 can include a syringe, a volumetric flask or a graduated cylinder, for example, for manual delivery, or an automatic syringe or a metering pump with associated plumbing and wiring, for example, for automatic delivery (as indicated in FIG. 5). For automatic delivery of water 121, the dilution device 120 can be connected, for example, to a pipe 123 running between the water reservoir 121 and the analysis cell 101. The computing device 151 can be operative to control the dilution device 120.

Suitable mechanisms 140 for measuring the concentration of fluoride ions in the test solution 102 preferably includes a fluoride ion specific electrode 141 and a reference electrode 142 in contact with the test solution 102, and a voltmeter 143 for measuring the potential between the two electrodes. Suitable reference electrodes and fluoride ion specific electrodes are well-known in the art and are available commercially. Typical reference electrodes include the silver-silver chloride electrode (SSCE), saturated calomel electrode (SCE), mercury-mercury sulfate electrode, for example. A double junction may be used for one or more electrodes to minimize contamination of the electrode solution by etchant solution species (which may cause drift in the electrode potential). The fluoride ion specific electrode 141 and the reference electrode 142 can be separate electrodes or can be combined in a combination electrode.

After a fluoride ISE measurement is completed, the test solution 102 is preferably flowed via a waste pipe 163 into a waste container 162. Between silicon determinations, the analysis cell 101 is preferably rinsed, e.g., with water. The analysis cell 101 can be rinsed using water provided by the dilution device 120 or by a separate rinse system. Waste 160 can be disposed.

Fluoride ISE calibrations and measurements should be performed at a constant temperature, preferably at or near room temperature, and/or fluoride ISE potentials should be corrected for significant variations in the temperature of the test solution 102. In certain embodiments, the apparatuses 10, 20, 30 and 40 of the present disclosure further includes a temperature sensor 180 for measuring the temperature of the test solution 102. The temperature sensor 180 can be of any suitable type, including a thermometer, a thermocouple (as indicated in FIG. 5), a thermistor, or an NIR spectrometer, for example. The computing device 151 can be operative to acquire temperature data from the temperature sensor 180 and correct the potentials measured for fluoride ion specific electrode 141 for temperature effects so as to provide a more accurate determination of the fluoride concentration in the test solution 102.

As silicon nitride etchant solutions operate at high temperature (>150° C.), a mechanism for rapidly cooling the predetermined volume of etchant solution 111 can significantly shorten the analysis time. Any suitable cooling mechanism can be used. For example, as indicated in FIG. 5, the etchant solution 111 flowed from the etchant tank 112 to the analysis cell 101 can be passed through a cooling device 183, which may include a jacketed portion of the pipe 113 or a heat radiator device, for example.

The apparatuses 10, 20, 30 and 40 of the present disclosure can preferably include a mechanism of controlling the temperature of the test solution 102 to minimize errors in the measured concentration of fluoride ions in the test solution. Suitable mechanisms for controlling the temperature of a liquid are well-known in the art and can include a hot plate or an immersion heater with feedback from a temperature sensor can be used to control the temperature of a liquid in an analysis cell. One mechanism of controlling the temperature of the test solution 102 is to pass water or another heat exchange liquid form a circulator/controller (or another constant temperature source) through a cooling jacket on the analysis cell 101.

The computing device 151 can include a computer with integrated components, or can include separate components, a microprocessor and a memory device that includes a memory element 152, for example. The memory element 152 can be any one of a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. The memory element 152 can be an integral part of the computing device 151 or can be a separate device.

In certain embodiments, various process tools can be used in connection with an analyzer and the methods and apparatuses of the present disclosure for measuring and monitoring multiple silicon forms. For example, and not by way of limitation, one or more process tools can supply a predetermined volume of an etchant solution to an analyzer. In certain embodiments, the one or more process tools can extract the predetermined volume of the etchant solution from a recirculation loop. The etchant solution extracted from the recirculation loop can be provided by the one or more process tools to the analyzer for testing. A person skilled in the art will appreciate that various process tools can be used in conjunction with analyzers and such apparatuses can be configured to numerous process systems.

The presently disclosed subject matter will be better understood by reference to the following Examples. The following examples are merely illustrative of the presently disclosed subject matter and should not be considered as limiting the scope of the subject matter in any way.

EXAMPLES

The following examples are merely illustrative of the presently disclosed subject matter and they should not be considered as limiting the scope of the subject matter in any way.

Example 1: Selective Measurement of Silicon Compounds (Fluoride Testing)

This Example evaluated selective measurement of two different silicon compounds (Compound A and Compound B) in an etchant solution using two fluoride testing methods. The two fluoride testing methods yielded different binding ratios for the same chemical and therefore provided for selective calculation of specific silicon compounds in solution.

Solutions 1-7 were prepared, each including blends of Compound A and Compound B as provided in Table 1 and were tested under two different experimental test conditions (Condition 1 and Condition 2). Compound B included silicon obtained from sodium silicate ($Na_2SiO_3$). Compound A included a silicon compound different than the silicon compound included in Compound B. Compound A included a silicon compound having at least one substituted (—OH) group in formula $Si(OH)_4$ (i.e., in formula Si—R1,R2,R3,R4, at least one of R1,R2,R3,R4 is not an —OH group). Solutions 1-7 were prepared and included varying concentrations of Compound A and Compound B as provided in Table 1. Table 1 provides the concentration of Compounds A and B in units of Si. For example, Si has an atomic weight of 28 and $Si(OH)_4$ has a formula weight of 96. Accordingly, 96 ppm of $Si(OH)_4$ compound↔28 ppm of Si. Solution 1 was a control solution. Solution 2 included approx. 50 ppm of Si from Compound B ($Na_2SiO_3$). Solution 3 included approx. 100 ppm of Si from Compound B ($Na_2SiO_3$). Solution 4 included approx. 150 ppm of Si from Compound A. Solution 5 included approx. 150 ppm of Si from Compound A and approx. 20 ppm of Si from Compound B ($Na_2SiO_3$). Solution 6 included approx. 75 ppm of Si from Compound A. Solution 7 included approx. 75 ppm of Si from Compound A and approx. 20 ppm of Si from Compound B ($Na_2SiO_3$). Each solution included approx. 85 wt.-% phosphoric acid ($H_3PO_4$), based on the total weight of the solution. Each solution was tested under two different experimental test conditions, Condition 1 and Condition 2, as provided below. After each condition, the total silicon concentration in the solution was measured via an analyzer. The analyzer measured the concentration in ppm of the Si element. The concentrations of each silicon compound (Compound A and Compound B) were selectively determined based on Equations 1-4 provided herein. As in Table 1, Table 2 provides the concentration of Compounds A and B in units of Si.

Condition 1 included methods described herein and as provided in U.S. Pat. No. 8,008,087 to Shalyt, et al. Condition 2 included a modified test condition in which deionized (DI) water was added in a quantity of 10.4 mL per 25 mL of each sample.

The fluoride binding ratio of Compound B was predetermined at 4.5 (i.e., Si*4.5F). The fluoride binding ratio of Compound A in Condition 1 was predetermined at 2 (i.e., Si*2F). The fluoride binding ratio of Compound A in Condition 2 was predetermined at 1.25 (i.e., Si*1.25F). This yielded $g_1=2/4.5=0.444$; $g_2=1.25/4.5=0.277$.

TABLE 1

| | Test Solutions | |
|---|---|---|
| Solution | Si from Compound A (ppm) | Si from Compound B ($Na_2SiO_3$) (ppm) |
| 1 | 0 | 0 |
| 2 | 0 | 50 |
| 3 | 0 | 100 |
| 4 | 150 | 0 |
| 5 | 150 | 20 |
| 6 | 75 | 0 |
| 7 | 75 | 20 |

The test results are provided in Table 2.

TABLE 2

Test Results

| Solution | Condition 1 Total Measured Silicon by Fluoride Method (ppm) | Condition 2 Total Measured Silicon by Fluoride Method (ppm) | Measured/Calculated Si from Compound A (ppm) | Measured/Calculated Si from Compound B ($Na_2SiO_3$) (ppm) |
|---|---|---|---|---|
| 1 | 0 | 0 | 0 | 0 |
| 2 | 50 | 50 | 0 | 50 |
| 3 | 100 | 100 | 0 | 100 |
| 4 | 67.58 | 42.03 | 150 | 0 |
| 5 | 83.83 | 60.03 | 139.70 | 20.89 |
| 6 | 31.83 | 19.23 | 73.93 | 0.48 |
| 7 | 50.73 | 36.49 | 83.53 | 13.09 |

Example 2: Selective Measurement of Silicon Compounds (Elemental Analysis and Fluoride Testing)

This Example evaluated selective measurement of two different silicon compounds (Compound A and Compound B) in an etchant solution using an elemental analysis method and a fluoride testing method. The elemental analysis of the solution provided a total concentration of a chemical such as Si with equal sensitivity to all forms. A fluoride test with different sensitivity to different forms of Si was used to calculate individual forms of the chemical in the solution.

Solutions 1-7 were prepared including varying concentrations of Compound A and Compound B as provided in Example 1. Each solution was tested under two different experimental test conditions, an elemental analysis method by inductively coupled plasma atomic emission spectroscopy (ICP-OES) (Avio 200, Perkin Elmer, Waltham, Mass.) and Condition 2 as provided in Example 1. The sample for ICP-OES analysis was prediluted to 1/10 with deionized water prior to measurement. The ICP-OES measurement was conducted at radial mode at a 251.6 nm wavelength.

After Condition 2, the total silicon concentration in the solution was measured via an analyzer. The analyzer measured the concentration in ppm of the Si element. The concentrations of each silicon compound (Compound A and Compound B) were selectively determined based on Equations 1-4 provided herein. In Equations 1-4, $g1=1$ since the ICP-OES elemental analysis used had equal sensitivity to all silicon compounds. Table 3 provides the concentration of Compound A and Compound B in units of Si.

The test results are provided in Table 3.

Example 3: Selective Measurement of Silicon Compounds (Measuring Method and Fluoride Testing)

This Example evaluates the selective measurement of two different silicon compounds (Compound A and Compound B) in an etchant solution using a measuring method and a fluoride testing method. The measuring method includes a method for measuring a specific functional group of silicon compounds. For example, the measuring method includes ultraviolet-visible near-infrared/infrared spectroscopy (UV-Vis-NIR-IR), Raman spectroscopy, potentiometry, voltammetry, surface tension, or chromatography. A fluoride test with different sensitivity to different forms of Si is used to calculate individual forms of the chemical in the solution.

Solutions 1-7 are prepared including varying concentrations of Compound A and Compound B as provided in Example 1. Each solution is tested under two different experimental conditions, a measuring method for measuring a specific functional group of silicon compounds and Condition 2 as provided in Example 1.

After Condition 2, the total silicon concentration in solution is measured via an analyzer. The analyzer measures the concentration in ppm of the Si element. The concentration of each silicon compound (Compound A and Compound B) are selectively determined based on Equations 1-4 provided herein. Specifically, the concentration of each silicon compound (Compound A and Compound B) is selectively determined according to either Method I or Method II.

Method I:

Elemental analysis (e.g., inductively coupled plasma atomic emission spectroscopy (ICP-OES)) measures the

TABLE 3

Test Results

| Solution | Total Measured Silicon by ICP-OES (ppm) | Condition 2 Total Measured Silicon by Fluoride Method (ppm) | Measured/Calculated Si from Compound A (ppm) | Measured/Calculated Si from Compound B ($Na_2SiO_3$) (ppm) |
|---|---|---|---|---|
| 1 | 0 | 0 | 0 | 0 |
| 2 | 56.29 | 50 | 8.74 | 47.55 |
| 3 | 104.43 | 100 | 6.16 | 98.27 |
| 4 | 153 | 42.03 | 154.17 | −1.17* |
| 5 | 171.84 | 60.03 | 155.33 | 16.51 |
| 6 | 80.36 | 19.23 | 84.92 | −4.56* |
| 7 | 99.62 | 36.49 | 87.7 | 11.92 |

*Negative calculated results should be interpreted as zero (within the detection limit)

total silicon (Si) concentration. Fluoride testing measures an "Effective Total Si 2" silicon concentration (i.e., total measured silicon). Equations 1-4 are solved to determine Si—X (e.g., Compound A) and Si—Y (e.g., Compound B).

Method II:

Measuring method (e.g., ultraviolet-visible near-infrared/infrared spectroscopy (UV-Vis-NIR-IR), Raman spectroscopy, potentiometry, voltammetry, surface tension, or chromatography) measures "X" to provide the quantity of Si—X in solution. Fluoride testing measures the "Effective Total Si 2" silicon concentration (i.e., total measured silicon). Equations 1-4 are solved to determined Si—X (e.g., Compound A) and Si—Y (e.g., Compound B).

The test results for the measured/calculated concentration of each silicon compound (Compound A and Compound B) in Solutions 1-7 are expected to be similar to the concentrations set forth in Example 1, Table 1, e.g., as calculated/measured in Example 1 (Table 2) by fluoride testing and Example 2 (Table 3) by elemental analysis and fluoride testing.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter. Moreover, the principles of the disclosed subject matter can be implemented in various configurations and are not intended to be limited in any way to the specific embodiments presented herein.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

What is claimed is:

1. A method for determining concentrations of a plurality of silicon compounds in an etchant solution, comprising:
   providing a test solution comprising a predetermined volume of an etchant solution, the etchant solution comprising a first silicon compound and a second silicon compound;
   adding a fluoride-based compound as a reagent to the test solution in a first condition, providing a first binding ratio of silicon:reagent, and performing a first measurement;
   adding the fluoride-based compound to the test solution in a second condition, providing a second binding ratio of silicon:reagent, and performing a second measurement; and
   determining a concentration of the first silicon compound and the second silicon compound based on the first and second measurements,
   wherein the first silicon compound is different than the second silicon compound, and
   wherein the first binding ratio is different than the second binding ratio.

2. The method of claim 1, wherein the fluoride-based compound includes a predetermined concentration of fluoride ions, and wherein performing the first and second measurements comprise measuring concentration of fluoride ions in the test solution; and determining a silicon concentration from the difference in the predetermined and the measured concentration of the fluoride ions in the test solution.

3. The method of claim 2, wherein the measuring concentration of the fluoride ions comprises using ion chromatography, capillary electrophoresis, or electrochemical methods.

4. The method of claim 3, wherein the measuring fluoride concentration of the fluoride ions comprises using a fluoride ion-selective electrode.

5. The method of claim 1, wherein the second condition includes adding a predetermined volume of a co-solvent to the test solution.

6. The method of claim 5, wherein the co-solvent is pre-blended with a reagent.

7. The method of claim 5, wherein the co-solvent is aqueous.

8. The method of claim 5, wherein the co-solvent includes deionized water.

9. The method of claim 5, wherein the co-solvent is non-aqueous.

10. The method of claim 9, wherein the co-solvent includes carboxylic acid, sulfonic acid, or a combination thereof.

11. The method of claim 10, wherein the co-solvent comprises acetic acid, propionic acid, methanesulfonic acid, substituted derivatives thereof, or combinations thereof.

12. The method of claim 1, wherein the test solution comprises phosphoric acid present in an amount of from about 10 wt.-% to about 100 wt.-%, based on the total weight of the test solution.

13. The method of claim 12, further comprising selectively etching silicon nitride with the test solution.

14. The method of claim 12, further comprising selectively etching a material with the test solution to manufacture a microelectronic device.

15. The method of claim 1, wherein providing the test solution comprises sampling the test solution from a recirculation loop.

16. A method for determining concentrations of a plurality of silicon compounds in an etchant solution, comprising:
   providing a test solution comprising a predetermined volume of an etchant solution, the etchant solution comprising a first silicon compound and a second silicon compound;
   adding a fluoride-based compound as a reagent to the test solution, providing a first binding ratio of silicon:reagent, and performing a first measurement;
   adding a predetermined volume of a co-solvent to the test solution, providing a second binding ratio of silicon:reagent, and performing a second measurement; and determining a concentration of the first silicon compound and the second silicon compound based on the first and second measurements, wherein the first silicon compound is different than the second silicon compound, and wherein the first binding ratio is different than the second binding ratio.

17. The method of claim 16, wherein the fluoride-based compound includes a predetermined concentration of fluoride ions, and wherein the performing the first and second measurements comprises measuring concentration of fluoride ions in the test solution; and determining a silicon concentration from the difference in the predetermined and the measured concentration of the fluoride ions in the test solution.

18. The method of claim 17, wherein the measuring concentration of the fluoride ions comprises using ion chromatography, capillary electrophoresis, or electrochemical methods.

19. A method for determining concentrations of a plurality of silicon compounds in an etchant solution, comprising:
providing a test solution having a first portion and a second portion and comprising a predetermined volume of an etchant solution, the etchant solution comprising a first silicon compound and a second silicon compound;
performing a first measurement of the first portion of the test solution, wherein the first measurement comprises a total silicon concentration or a total concentration of one or more functional groups of a silicon form of the first or second silicon compound;
adding a fluoride-based compound as a reagent to the second portion of the test solution, and providing a binding ratio of silicon:reagent;
performing a second measurement; and
determining a concentration of the first silicon compound and the second silicon compound based on the first and second measurements.

20. The method of claim 19, wherein the fluoride-based compound includes a predetermined concentration of fluoride ions, and wherein performing the second measurement comprises measuring concentration of fluoride ions in the test solution; and determining a silicon concentration from the difference in the predetermined and the measured concentration of the fluoride ions in the test solution.

21. The method of claim 20, wherein the measuring concentration of the fluoride ions is selected from the group consisting of using ion chromatography, capillary electrophoresis, or electrochemical methods.

22. The method of claim 19, wherein performing the first measurement comprises having equal sensitivity to all silicon forms, and performing the second measurement comprises having unequal sensitivity to all silicon forms.

23. The method of claim 19, further comprising diluting the first portion of the test solution prior to performing the first measurement.

24. An apparatus for determining concentrations of a plurality of silicon compounds in an etchant solution comprising phosphoric acid, silicon compounds and water, comprising:
an analysis cell adapted to contain a test solution comprising a predetermined volume of the etchant solution, a predetermined concentration of a fluoride-based reagent, and optionally a predetermined volume of a co-solvent;
a reservoir, fluidically coupled to the analysis cell, adapted to receive the predetermined volume of the etchant solution, the predetermined concentration of the fluoride-based reagent, and the predetermined volume of the co-solvent;
a fluoride ion specific electrode and a reference electrode operatively coupled to the analysis cell for measuring the concentration of fluoride ions in the test solution; and
a processor having a memory element with stored instructions operative to cause, when executed,
providing the predetermined volume of the etchant solution from the reservoir to the analysis cell,
providing the predetermined volume of the co-solvent, if any, from the reservoir to the analysis cell,
providing the predetermined concentration of the fluoride-based reagent from the reservoir to the analysis cell in stoichiometric excess at a predetermined binding ratio of that required to react with substantially all silicon ions in the test solution such that the fluoride ion specific electrode and the reference electrode contact with the test solution,
measuring a potential of the fluoride ion specific electrode, and
determining the concentration of silicon ions in the etchant solution based on the difference in the measured potential and an expected potential for the predetermined concentration of the fluoride ions in the test solution.

25. The apparatus of claim 24, wherein the fluoride ion specific electrode and the reference electrode comprise a combination electrode, and fluoride ions are added to the test solution as part of a fluoride compound.

26. The apparatus of claim 24, further comprising a temperature sensor for measuring a temperature of the test solution, wherein the processor is further operative to acquire temperature data from the temperature sensor.

27. An apparatus for determining concentrations of a plurality of silicon compounds in an etchant solution comprising phosphoric acid, silicon compounds and water, comprising:
an analysis cell adapted to contain a test solution comprising a predetermined volume of the etchant solution and a predetermined volume of a co-solvent, the co-solvent comprising a predetermined concentration of a fluoride-based reagent;
a reservoir, fluidically coupled to the analysis cell, adapted to receive the predetermined volume of the etchant solution to the test solution and the predetermined volume of the co-solvent;
a fluoride ion specific electrode and a reference electrode operatively coupled to the analysis cell for measuring the concentration of fluoride ions in the test solution; and
a processor having a memory element with stored instructions operative to cause, when executed,
providing the predetermined volume of the etchant solution from the reservoir to the analysis cell,
providing the predetermined volume of the co-solvent from the reservoir to the analysis cell, the co-solvent comprising the predetermined of the fluoride-based reagent in stoichiometric excess at a predetermined binding ratio of that required to react with substantially all silicon ions in the test solution such that the fluoride ion specific electrode and the reference electrode contact with the test solution,
measuring a potential of the fluoride ion specific electrode, and determining the concentration of silicon ions in the etchant solution based on the difference in the measured potential and an expected potential for the predetermined concentration of the fluoride ions in the test solution.

28. An apparatus for determining concentrations of a plurality of silicon compounds in an etchant solution comprising phosphoric acid, silicon compounds and water, comprising:

a first analysis cell adapted to contain a first test solution comprising a predetermined volume of the etchant solution and a predetermined volume of a co-solvent, the co-solvent comprising a predetermined concentration of a fluoride-based reagent;

a second analysis cell adapted to contain a second test solution comprising a predetermined volume of the etchant solution;

a reservoir, fluidically coupled to the first and second analysis cells, adapted to receive the predetermined volume of the etchant solution to the first and second test solutions;

a fluoride ion specific electrode and a reference electrode operatively coupled to the first analysis cell for measuring the concentration of fluoride ions in the first test solution;

an elemental analyzer operatively coupled to the second analysis cell for measuring the total silicon concentration of the second test solution; and a processor having a memory element with stored instructions operative to cause, when executed, providing the predetermined volume of the etchant solution from the reservoir to the first and second analysis cells, providing the predetermined volume of the co-solvent from the reservoir to the first analysis cell, the co-solvent comprising the predetermined concentration of the fluoride-based reagent in stoichiometric excess at a predetermined binding ratio of that required to react with substantially all silicon ions in the test solution such that the fluoride ion specific electrode and the reference electrode contact with the first test solution, measuring a potential of the fluoride ion specific electrode, determining the concentration of silicon ions in the first etchant solution based on the measured potential and an expected potential for the predetermined concentration of the fluoride ions in the first test solution, and providing a predetermined volume of the second test solution from the second analysis cell to the elemental analyzer for elemental analysis, and determining a total silicon concentration of the second test solution.

* * * * *